United States Patent
Kasemo et al.

(10) Patent No.: US 9,638,633 B2
(45) Date of Patent: May 2, 2017

(54) SURFACE PLASMON RESONANCE GAS SENSOR, GAS SENSING SYSTEM, AND GAS SENSING METHOD

(71) Applicant: INSPLORION SENSOR SYSTEMS AB, Göteborg (SE)

(72) Inventors: Bengt Herbert Kasemo, Köpmannebro (SE); Christoph Langhammer, Göteborg (SE); Ferry Anggoro Ardy Nugroho, Göteborg (SE)

(73) Assignee: INSPLORION SENSOR SYSTEMS AB, Gothenburg (SE)

( * ) Notice: Subject to any disclaimer, the term of this patent is extended or adjusted under 35 U.S.C. 154(b) by 0 days.

(21) Appl. No.: 15/105,408

(22) PCT Filed: Dec. 18, 2014

(86) PCT No.: PCT/EP2014/078484
§ 371 (c)(1),
(2) Date: Jun. 16, 2016

(87) PCT Pub. No.: WO2015/091811
PCT Pub. Date: Jun. 25, 2015

(65) Prior Publication Data
US 2016/0320300 A1    Nov. 3, 2016

(30) Foreign Application Priority Data
Dec. 19, 2013   (EP) ..................................... 13198508

(51) Int. Cl.
*G01N 21/00*    (2006.01)
*G01N 21/552*    (2014.01)
*G01N 33/00*    (2006.01)

(52) U.S. Cl.
CPC ....... *G01N 21/554* (2013.01); *G01N 33/0036* (2013.01); *G01N 2201/061* (2013.01)

(58) Field of Classification Search
CPC ........... G01N 21/554; G01N 2201/061; G01N 33/0036
See application file for complete search history.

(56) References Cited

U.S. PATENT DOCUMENTS

2011/0205543 A1* 8/2011 Offermans ........... G01N 21/554
356/445

FOREIGN PATENT DOCUMENTS

WO    WO-2010136440 A1    12/2010

OTHER PUBLICATIONS

International Search Report and Written Opinion mailed Mar. 18, 2015 for PCT Application No. PCT/EP2014/078484.

* cited by examiner

*Primary Examiner* — Michael P Stafira
(74) *Attorney, Agent, or Firm* — Moser Taboada (57) ABSTRACT

The present invention relates to a gas sensor comprising a sensor layer (100) comprising a plasmonic sensor (102) provided so as to allow, upon illumination with electromagnetic radiation a localized surface plasmon resonance condition, a sensing layer (106) comprising a gas permeable material that, when exposed to a gas, modifies the localized surface plasmon resonance condition, a separating layer (104) arranged in between the sensor layer (100) and the sensing layer (106) such that the plasmonic sensor (102) is separated from the sensing layer (106). A gas sensing system and a method for sensing a presence of a gas is further disclosed.

15 Claims, 5 Drawing Sheets

SURFACE PLASMON RESONANCE GAS SENSOR, GAS SENSING SYSTEM, AND GAS SENSING METHOD

FIELD OF THE INVENTION

The present invention relates to sensing of gas, and in particular to a gas sensor, a gas sensing system and a method for measuring a presence of a gas.

BACKGROUND OF THE INVENTION

Gas detection is of importance in a wide range of applications. Petrochemical industries, for example, where safety issues are of particular importance, utilize gas sensors for detection of toxic or flammable gases. Gas sensors are used in process industries to monitor feedstock and measure the abundance of specific gases used or formed during production. In catalytic exhaust cleaning, for instance, gas sensors facilitates simultaneous conversion of $NO_x$ to $N_2$ and CO to $CO_2$ and hydrocarbons to $H_2O$ and $CO_2$. The use of highly sensitive gas detectors is also widespread in atmospheric science, where they are used to measure and understand the abundance and the pathways of various gas species including greenhouse gases. Reliable gas detection is also beneficial for improved monitoring and analysis of biomarker gases such as nitric oxide, ethane, ammonia etc. during, for example, breath diagnostics.

Qualitative as well as quantitative detection of gases is traditionally performed using conventional laboratory analytical equipment such as optical spectrometers, chromatographs, mass spectrometers as well as semiconductor based gas sensors or electrochemical devices.

The range of applications for gas sensors is constantly increased. In connection with the International Climate Change Panel, ICCP, for example, prognoses for temperature increase and climate change, mainly due to carbon dioxide emission, have intensified efforts to develop techniques for capturing and storage of carbon dioxide. Hence there is an increased need for efficient detection and monitoring of gases such as carbon dioxide, in particular within gas storage media. To this end, there are currently two dominating detection techniques for detecting the presence of carbon dioxide: non-dispersive infrared (NDIR) and chemical sensors. The former relies on the detection of the vibrational modes of carbon dioxide molecules, which are located in the IR range. The latter is based on chemical interactions or reactions that are triggered by the existence of carbon dioxide. These detection techniques have in common that they rely on relatively delicate instrumentation that is relatively large and costly and is difficult to scale down. Hence there is a need to improve gas sensors in general and in particular to provide smaller gas sensors that are efficient in sensing gas.

US 2011/0205543 discloses such a gas sensor comprising a first layer including an array of nanoparticles, and a second layer including a material, which has a porosity of at least 10%. The nanoparticles are provided so as to allow, upon illumination with electromagnetic radiation, long range diffractive coupling of surface plasmon resonances resulting in a surface lattice resonance condition. When the gas sensor is exposed to at least one predetermined gas the surface lattice resonance condition is detectably changed whereby the gas is sensed.

There is, however, a need for improved gas sensors, which are more reliable and robust.

SUMMARY OF THE INVENTION

An object of the present invention is to solve or at least to reduce the problems discussed above.

According to a first aspect of the invention, a gas sensor is provided. The gas sensor comprises, a sensor layer comprising a plasmonic sensor provided so as to allow, upon illumination with electromagnetic radiation a localized surface plasmon resonance condition, a sensing layer comprising a gas permeable material that, when exposed to a gas, modifies the localized surface plasmon resonance condition, a separating layer arranged in between the sensor layer and the sensing layer such that the plasmonic sensor is separated from the sensing layer.

This arrangement of the layers of the gas sensor is advantageous as a more reliable and stable gas sensor is provided. The gas sensor is moreover compact and has a low cost and low complexity.

The separating layer protects the plasmonic sensor of the sensor layer from being in direct contact with the sensing layer. The separating layer may further prevent the plasmonic sensor from reacting with gas present in the sensing layer and/or in the environment of the gas sensor. Structural reshaping and/or other reactions such as oxidation or corrosion of the plasmonic sensor may thereby be further mitigated. This is advantageous as it is known that changes to the shape and/or size and/or chemical composition of the plasmonic sensor may change the local surface plasmon condition of the plasmonic sensor.

The arrangement according to the present invention may be described as an indirect gas sensor utilizing the plasmonic sensor. In other words, the gas sensor is indirect as the plasmonic sensor is separated from the sensing layer comprising the gas by the separating layer.

The wording plasmonic sensor should be construed as a sensor in which plasmons may be excited. Plasmons should here be understood as quanta of plasma oscillations associated with a local collective oscillation of charge density. The charges may for instance be provided by electrons within the conduction band of the material of the plasmonic sensor.

The wording localized surface plasmon resonance LSPR is to be understood as an excited state of the charge carriers within the plasmonic sensor, which can be excited by photons or, equivalently, by the electromagnetic field of light incident on the plasmonic sensor. The LSPR condition is a resonance condition associated to the collective oscillation of charge density and to the boundary conditions resulting from the finite size of the plasmonic sensor. As a result, a charge density wave is formed with a frequency/wavelength/energy that is set by the electronic properties of the material of the plasmonic sensor, its geometry, size and the material properties of the environment surrounding the plasmonic sensor. As an example, the LSPR typically occurs in the visible part of the electromagnetic wavelength spectrum if the plasmonic sensor is a gold nanoparticle having a diameter in the range of 50-100 nm.

It should further be understood that the LSPR occurs when the electromagnetic radiation interacts with the plasmonic sensor. As a result an enhanced local electromagnetic field is created in the close vicinity of the plasmonic sensor. The strength of the enhancement and the spatial extent of the enhanced field depend on a number of parameters such as the material, size, shape, and environment of the plasmonic sensor. The enhanced electric field is beneficial as it improves the sensitivity of the plasmonic sensor such that a more efficient gas sensor is provided.

The gas permeable material may comprise a porous material. The wording porous material should be construed as a material comprising pores, i.e., voids, cavities, channels and/or, interstices. The porous material of the sensing layer may according to the present invention comprise pores being closed, open, blind, and/or through pores as long as the porous material enables penetration of gases through the sensing layer. The porous material is advantageous to use as it provides a large surface to volume ratio for gas adsorption. As a result the change of the LSPR condition is increased and a more efficient gas sensor is provided.

It has further been found that when gas enters the porous material, the refractive index and/or the extinction coefficient of the porous material may change. This leads to a detectable change in the LSPR condition of the plasmonic sensors of the sensor layer. Furthermore, the optical properties of the porous material may not only change by the presence of gases, but may also change due to the gas reacting with or being adsorbed in the porous material.

The porous material may be selected from a group of porous materials consisting of macroporous, mesoporous, microporous, and hybrid porous materials.

The porous materials may be classified into several categories depending on the average pore size of the porous material. According to International Union of Pure and Applied Chemistry (IUPAC), for instance in Pure Appl. Chem., Vol. 73, No. 2, pp. 381-394, 2001, microporous materials are to be understood as materials having pore diameters of less than 2 nm and macroporous materials having pore diameters of greater than 50 nm. The mesoporous category thus lies in between the microporous and macroporous categories.

Hybrid porous materials should further be understood as mesoporous organic-inorganic hybrid materials characterized by large specific surface areas and pore sizes typically between 2 nm and 15 nm, which have been obtained through the coupling of inorganic and organic components. In other words, hybrid porous materials results from the reaction between organic and inorganic species in order to build up three-dimensional frameworks.

The person skilled in the art realizes that the categories of the porous materials provided above should not be understood as strict definitions. For example, in other definitions of the different categories the particle sizes dividing the porous materials into the different categories may vary.

For example, the porous material may be characterized as a nanoporous material. Nanoporous materials are often defined as porous materials having pore sizes about 100 nanometer or smaller, down to ca 1 nanometer, and may comprise organic and/or inorganic frameworks supporting a porous structure. Hence, according to this definition a nanoporous material may fall into at least one of the categories macroporous, mesoporous, microporous and hybrid porous materials.

It should be noted that the porous material may also have pore sizes larger than 1 micrometer.

By selecting a porous material from the disclosed categories of porous materials it may be possible to tailor the adsorption and penetration of gases in and through the sensing layer. An improved selectivity of the gas sensor may thereby be obtained.

The gas permeable material may comprise a polymer. The polymer may be a non-porous material, which, however, when in contact with a gas changes its material structure and/or composition such that the polymer becomes permeable to the gas. The gas may thereby penetrate through the sensing layer comprising the polymer. Different polymers are permeable to different gases. This is advantageous as improved gas selectivity of the gas sensor may be obtained.

The gas may comprise a gas selected from a group consisting of carbon oxides, nitrogen oxides, oxygen, ozone, nitrogen, hydrogen, water vapour, sulphur oxides, hydrocarbons, ammonia, ethane, and halogens.

Hence a more versatile gas sensor may be provided. It should be noted that the gas may comprise a composition of different gases. The given name of a gas disclosed above should be interpreted in its broadest sense. Carbon oxides should, for example, be understood to comprise carbon monoxide, carbon dioxide and nitrogen oxides di-nitrogen oxide, nitrogen oxide, and nitrogen di-oxide etc.

The modification of the localized surface plasmon resonance condition may result in a change of at least one of a spectral shift of resonance frequency, an amplitude shift of optical cross-section, and a change of damping of the localized surface plasmon resonance condition.

This is beneficial as a sensitive and an efficient detection of a change of the LSPR condition may be provided, for instance, by conventional optical characterization techniques.

The plasmonic sensor may be a disk, rod, wire, ellipse, polygon, triangle, sphere, cube, star, hole in thin metal film, nanoshell, core-shell particle, nanorice or nanoring.

The plasmonic sensors may comprise a semiconductor and/or a metal. It is understood that the semiconductor should comprise a plurality of free charge carriers, i.e. electrons and/or holes such that the semiconductor plasmonic sensor may provide a LSPR condition. This may for instance be achieved by doping the semiconductor.

The semiconductor material may for instance comprise silicon, germanium, carbon and/or III-V semiconductor materials. These are all known materials in material science and semiconductor technology, which facilitates the fabrication of the gas sensor as for instance standard epitaxial growth and processing techniques may be used.

The metal may further be selected from a group consisting of Ag, Au, Cu, Al, Mg, Ni, Pd and Pt, or alloys comprising at least one metal selected from the group. These materials are known to provide LSPRs in the ultra violet-visible-near infrared UV-vis-NIR wavelength ranges of the electromagnetic spectrum. Hence standard optical techniques may be used to excite and detect LSPRs of the plasmonic sensors.

The optical properties of the gas sensor may be changed by varying, in accordance with the disclosed materials, shapes and/or dimensions of the plasmonic sensors given above. Hence the LSPR condition may be tuned such that the specific optical wavelength for which the LSPR occurs is provided in a desired wavelength range.

The separating layer may comprise a material selected from a group of materials comprising a metal oxide, a metal carbide or a metal nitride; a semiconductor oxide or a semiconductor nitride or a semiconductor carbide; an insulator, and a polymer. An advantage of the present invention is its versatility since basically any sample material and form of sample material can be applied onto the separating layer that is protecting the plasmonic sensor from gases within the sensing layer.

The gas sensor may further comprise a plurality of plasmonic sensors, which may increase the reliability and selectivity of the gas sensor.

According to a second aspect of the invention, a gas sensing system is provided. The gas sensing system comprises a gas sensor according to the first aspect of the invention, a source of electromagnetic radiation for illuminating the gas sensor; and a detector for detecting electromagnetic radiation that is being scattered and/or reflected by and/or transmitted through the gas sensor, a processing unit arranged to determine changes in the scattered and/or reflected and/or transmitted electromagnetic radiation caused by a change in the localized surface plasmon resonance condition when the sensing layer is exposed to a gas.

The gas sensing system may thereby take advantage of the reliability and robustness of the gas sensor when sensing gas. An efficient system for monitoring LSPR and changes to the LSPR is furthermore provided by detecting electromagnetic radiation that is being scattered and/or reflected by and/or transmitted through the gas sensor. The gas sensing system may further offer remote real time gas sensing, using for instance conventional optical characterization techniques such as transmission and/or reflection measurements.

The gas sensing system may further comprise a temperature and/or pressure sensor. This is advantageous as independent measurements of the temperature and/or the pressure may be used to gain further information about the processes such as adsorption, desorption, oxidation and catalytic reactions occurring within the sensor and/or in the environment where the gas sensing system is used.

According to a third aspect of the invention, a method for sensing a presence of a gas is provided. The method comprises illuminating a gas sensor according to the first aspect of the invention with electromagnetic radiation from a electromagnetic radiation source; detecting, via a electromagnetic radiation detector, electromagnetic radiation that is being scattered and/or reflected by and/or transmitted through the gas sensor, analysing, by means of a processing unit, changes in the scattered and/or reflected and/or transmitted electromagnetic radiation caused by a modification of the localized surface plasmon resonance condition when the sensing layer is exposed to the gas.

In general, features of the aspects of the invention provide similar advantages as discussed above in relation to the previous aspect of the invention.

Further features of, and advantages with, the present invention will become apparent when studying the appended claims and the following description. The skilled person will realize that different features of the present invention may be combined to create embodiments other than those described in the following, without departing from the scope of the present invention.

BRIEF DESCRIPTION OF THE DRAWINGS

This and other aspects of the present invention will now be described in more detail, with reference to the appended drawings showing embodiments of the invention. The figures should not be considered limiting to the invention to the specific embodiment; instead they are used for explaining and understanding the invention.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

The basic idea of this invention is to provide a gas sensor, which uses a plasmonic sensor to sense gas in a sensing layer comprising a gas permeable material. The plasmonic sensor shows, upon illumination with electromagnetic radiation, such as visible or near visible light, a localized surface plasmon resonance, LSPR, condition. Gas within the gas permeable material is sensed by detecting changes in the LSPR condition. A change of the LSPR is a result of the local environment of the plasmonic sensor being changed or that the shape and/or structure of the plasmonic sensor itself is changed by the presence of gas. According to the invention a separating layer is provided and arranged to separate the plasmonic sensor from gas present in the sensing layer. A more reliable and robust sensor is thereby provided. By tailoring the size, shape and material of the plasmonic sensor and the separating layer it is further possible to tune the LSPR condition such that a more efficient gas sensor is provided as will be described in detail below.

Figure 1:
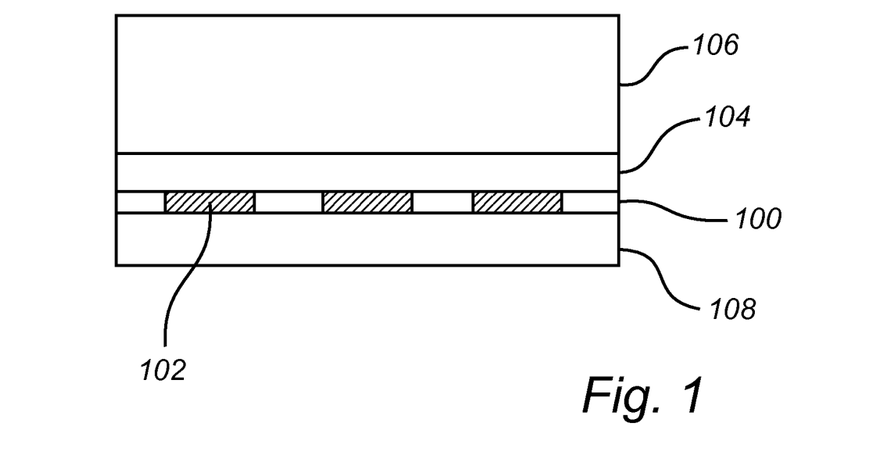
FIG. 1 is a schematic side view of a gas sensor according to one embodiment of the invention.

Next, a gas sensor 10 according to an embodiment of the present invention will be described with reference to FIG. 1. FIG. 1 shows a gas sensor 10, which comprises a sensor layer 100 with a plurality of plasmonic sensors 102, a separating layer 104, and sensing layer 106. The gas sensor 10 is further arranged on a substrate 108. The substrate 108 provides easy handling of the gas sensor 10. According to this embodiment the plasmonic sensors 102 are gold nanodiscs having a diameter of 110 nm and a thickness of 20 nm. Moreover, the separating layer 104 is made of compact titanium dioxide $TiO_2$, whereas the sensing layer 106 comprises porous sputtered $TiO_2$. The substrate 108 is made of transparent soda lime glass. These materials are chosen in order to provide an efficient gas sensor 10 comprising plasmonic sensors 102 which have LSPR conditions such that their resonances occur in the visible or near visible regions of the electromagnetic spectrum. It should be noted that this is one embodiment of the present invention. Other embodiments of the present invention will be exemplified in the following.

The gas sensor 10 may be manufactured by providing the plasmonic sensors 102 on soda lime glass slides, for instance by hole-mask colloidal lithography or electron beam lithography techniques. The compact $TiO_2$ layer has a thickness of 12 nm and was deposited on top of the gold nanodiscs by use of reactive sputtering from a Ti target, using, for instance, a FHR MS150 sputter system. The porous sensing layer 106 of $TiO_2$ was provided on top of the plasmonic sensor 102 by screen printing of a colloidal $TiO_2$ paste onto the compact $TiO_2$ layer, i.e. the separating layer 104. The gas sensor 10 was together with the substrate 108 subsequently sintered at 500° C. for 1 h in air, which results in that the $TiO_2$ layer of the sensing layer 106 reaches a thickness of about 10 micrometer. The porous structure of the fabricated porous $TiO_2$ layer 106 further has an average particle size of 20 nm, an average pore size of 23 nm, and a porosity of 69%. Hence, the porous $TiO_2$ layer is permeable to gases such as carbon oxides, e.g. $CO_2$ or CO and nitrogen oxides, e.g. $NO_x$.

According to other embodiments, the average pore size and the porosity may be different from the above given values. In some applications, it may for instance be advantageous to increase the inner surface of the porous material in order to allow for a larger amount of gas to be adsorbed or absorbed within the porous material. This may for instance be achieved by reducing the pore size of the porous material. By reducing the pore size a slower response time of the gas sensor may be obtained as the time for the gas to penetrate the porous material may be increased. This is beneficial when for instance acquiring information about the gas diffusion rate within the porous material.

By increasing the pore size of the porous material a faster response time of the gas sensor may be obtained.

The $TiO_2$ layer of the separating layer 104 is made compact such that the gas cannot penetrate the separating layer 104. The plasmonic sensors 102 are thereby protected from being in physical contact with the gas. The thickness of the separating layer 104 is, however, made thin enough such that the plasmonic sensors 102 may sense the presence of gas in the sensing layer 106. In other words, local electromagnetic EM fields, pertaining to the excited plasmonic sensors, extend at least a few tens of nanometers into the sensing layer 106 such that a change of the material properties of the sensing layer 106 affects the LSPR condition of the plasmonic sensors 102. The presence of the gas in the sensing layer 106 may thereby be sensed by the plasmonic sensors 102, by for instance optical means as will be described below.

The separating layer 104 described above may in other embodiments be a few nanometer to a few tens of nanometer thick "coating" of the plasmonic sensors 102 which protects the plasmonic sensors 102 from directly reacting with their environment, i.e. the environment in which the gas sensor is used but also gases within the sensing layer 106. Structural reshaping and/or other reactions such as oxidation or corrosion of the plasmonic sensors 102 may thereby be mitigated. This is advantageous as variations in the shape and/or size of the plasmonic sensors 102 may change the LSPR condition of the plasmonic sensors 102. Hence a more reliable and robust gas sensor 100 may be provided.

According to other embodiments of the invention the separating layer may have a thickness in the range of 0.5 to 150 nanometer.

It should be noted that in other embodiments, the separating layer may only protect the plasmonic sensors from being in direct contact with the sensing layer. The separating layer may hence allow at least one gas to come in direct contact with the plasmonic sensors. This may for instance be achieved by providing a separating layer that is gas permeable to the at least one gas. Hence a gas sensor with increased selectivity may be obtained as will be exemplified below.

The separating layer may comprise a material selected from a group of materials comprising oxides of metals such as aluminium, magnesium, tantalum, beryllium, barium, cerium; nitrides of metals such as titanium, aluminium; carbides of metals such as tungsten, titanium; sulphides of metals such as molybdenum and furthermore oxides of semiconductors such as silicon, and germanium; carbides of semiconductors such as silicon and nitrides of semiconductors such as silicon and gallium arsenide, and polymers such as poly(hydrogenmethylsiloxane) PHMS, Poly(dimethylsiloxane) PDMS or Poly(methylmethacrylate) PMMA.

The separating layer may further be used to provide a desired surface chemistry such that the manufacturing of the gas sensor is made more efficient. The separating layer may be provided with different functionalities related to the particular use of the gas sensor and the particular gas sensing layer used in the gas sensor. For example, it may be desirable to provide a surface functionality, i.e. surface chemistry, of the separating layer, such that the gas permeable material of the sensing layer is well attached to the separating layer and does not come loose during operation of the gas sensor.

According to one embodiment of the present invention the separating layer may comprise a plurality of layers, for example one layer providing impermeability to a gas and one providing good attachment to the sensing layer.

PHMS polymers that may easily be spin-coated in very thin layers are examples of materials, which are advantageous to use as a separating layer. PHMS is however permeable to many gases, but by heating such the PHMS layer to ca 300° C. or by plasma oxidizing the surface of the PHMS a $SiO_2$ layer is formed by oxidation on the PHMS layer such that the PHMS layer may become impermeable to gases.

The porous material of the sensing layer may comprise materials selected from a group consisting of oxides of niobium, tantalum, titanium, silicon, zirconium, cerium and tin; metal organic frameworks (MOFs); zeolites; hybrid porous materials and amine-impregnated materials. The porous materials may have a disordered and/or ordered material structure.

According to one embodiment of the present invention, the porous material may comprise a plurality of particles, which may be of the same material, size, or shape, or differ. The porous material may comprise particles that are for instance 100 nanometer in diameter or larger that are packed together, and particles that are smaller such that they may be arranged at interstitial spaces of the packed particles. The smaller particles thereby reduce the pores sizes of the porous material. By adding yet smaller particles even smaller pores may be formed. A porous material may thereby be formed in which the porosity may be changed by changing the sizes the particles. By such arrangements the porosity of the porous material may be reduced successively, but without losing permeability. The surface area of the porous material may further be increased which may increase the gas adsorption of the porous material. Hence the sensitivity of the gas sensor may be increased. The use of small pores may further be advantageous as it is facilitates the prevention of larger gas molecules to penetrate through the porous material. In other words, only smaller gas molecules are sensed by such a gas sensor as only the smaller gas molecules may reach close enough, typically in the order of 100 nm, to the plasmonic sensors.

The gas comprises a gas selected from a group consisting of carbon oxides, nitrogen oxides, oxygen, ozone, nitrogen, hydrogen, water vapour, sulphur oxides, hydrocarbons, ammonia, ethane, and halogens. A person skilled in the art should understand that other gases and gas mixtures may also be sensed.

According to other embodiments the plasmonic sensors may have dimensions in the range 5-500 nm in a direction parallel to the surface of layers of the gas sensor 100. The height of the sensors may also vary in the range of 5-100 nm.

The plasmonic sensors may according to other embodiments be shaped as a rod, wire, ellipse, polygon, triangle, sphere, cube, star, hole in thin metal film, nanoshell, core-shell particle, nanorice or nanoring.

The plasmonic sensors may comprise a semiconductor and/or a metal. It is understood that the semiconductor comprises a plurality of free charge carriers i.e. electrons and/or holes such that the semiconductor bases plasmonic sensor may provide a LSPR condition. This may for instance be achieved by doping of the semiconductor. The semiconductor material may for instance comprise silicon, carbon and/or III-V semiconductor materials. These are all known material in material sciences and semiconductor technology, which facilitates the fabrication of the gas sensor as for instance standard epitaxial growth and processing techniques may be used.

The metal may further be selected from a group consisting of Ag, Cu, Al, Mg, Ni, Pd and Pt, or alloys comprising at least one metal selected from the group. These materials are known to provide LSPRs in the ultra violet-visible-near infrared UV-vis-NIR wavelength ranges of the electromagnetic spectrum. Hence standard optical techniques may be used to excite and detect LSPRs of the plasmonic sensors, which simplify the detection of changes in the LSPR condition caused by the gas present in the sensing layer.

The person skilled in the art should understand that other metals providing LSPRs may also be used.

The person skilled in the art further realizes that the electromagnetic properties of the gas sensor may be changed by varying, in accordance with the disclosed materials, shapes and/or dimensions of the plasmonic sensors given above. Hence the LSPR condition may be tuned such that the specific optical wavelength for which the LSPR occurs is provided at a suitable wavelength range.

To this end the gas sensor may comprise a plurality of plasmonic sensors of different materials and having different shapes, and/or dimensions.

Figures 2A, 2B:
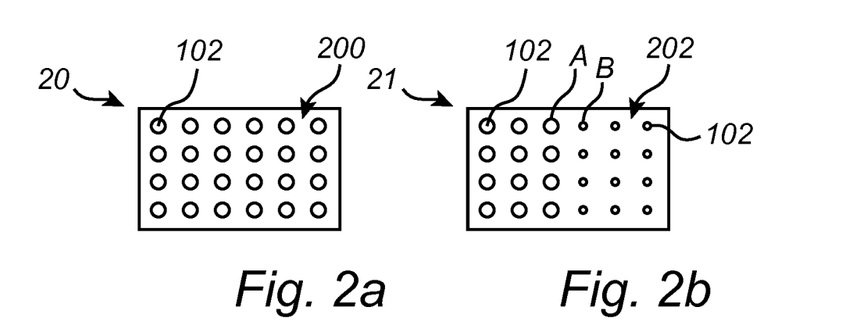
FIGS. 2a-c are schematic top views, of gas sensors according to different embodiments of the invention.
Figure 2C:
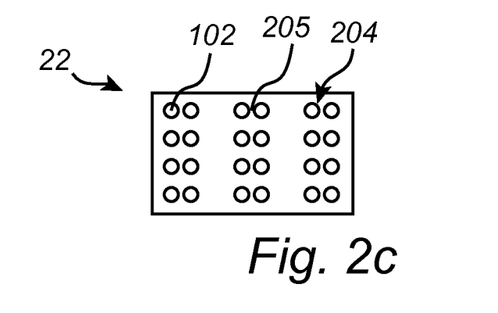

FIGS. 2a, 2b and 2c show top views of gas sensors 20, 21, 22 comprising a plurality of plasmonic sensors 102 arranged in the arrays 200, 202, and 204, respectively. The sensing layer and the separating layer of the gas sensors 20, 21, 22 are, for clarity, not shown in these figures. By providing a plurality of plasmonic sensors 102 inhomogeneities in for instance the size and shape of individual plasmonic sensors 102 may be averaged out. As a result an average or effective LSPR condition for the arrays 200, 202, 204 of plasmonic sensors 102 may be obtained. By measuring changes to the average LSPR condition a more reliable gas sensor may be obtained. The array 200 of plasmonic sensors 102 may moreover provide a larger area for sensing gas. Hence a more efficient gas sensor may be provided.

In FIG. 2b an array 202 of plasmonic sensors 102 is shown. The array 202 comprises a plurality of plasmonic sensors 102 being of type A and B. The type A and type B plasmonic sensors 102 are illustrated to have different diameters resulting in that the LSPR conditions of the respective plasmonic sensors 102 are shifted in wavelength. Two different channels for measuring the presence of gas are thereby, provided which improves the reliability and the sensitivity of the gas sensor.

According to other embodiments the type A and type B plasmonic sensors may differ by other parameters such as shape, size, and/or material, which alter the LSPR condition of the respective plasmonic sensors 102.

FIG. 2c shows an array 204 of plasmonic sensors 102 where the separation between the plasmonic sensors 102 is made small enough such that the plasmonic sensors 102 are electromagnetically coupled. A gap 205 is thereby provided in which the coupling may increase the local electromagnetic field. The sensitivity of the gas sensor may thereby be improved. The coupling of the plasmonic sensor may further shift the LSPRs of the plasmonic sensors 102 providing an additional means to shift or tune the LSPR conditions.

The gas sensor may according to other embodiments of the present invention comprise arrays of plasmonic sensors wherein the plasmonic sensors are arranged randomly and/or in patterns other than the ones disclosed above. The arrays may comprise plasmonic sensors of differing materials, sizes and or shapes. By changing the array of the plasmonic sensors, for instance the size and and/or the pitch of the arrays, the spectral position of the LSPRs may be shifted. In other words, the LSPR conditions are selected such that the resonances cover a wavelength range of interest. Thus, upon gas exposure, the resonance condition of an array of plasmonic sensors changes due to the increase or decrease of the refractive index or changes extinction cross-section of the sensing material.

Figure 3:
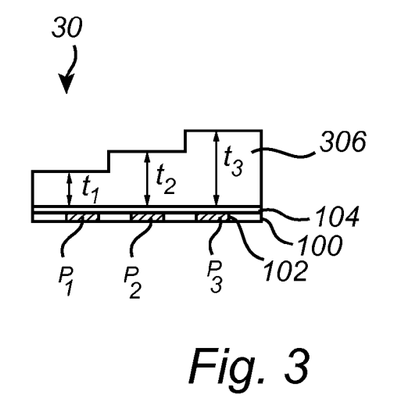
FIG. 3 is a schematic side view of a gas sensor according to one embodiment of the invention.

FIG. 3 illustrates a side view of a gas sensor 30, according to an embodiment of the present invention. The gas sensor 30 comprises a plurality of plasmonic sensors 102, denoted $P_1$, $P_2$, and $P_3$, in a sensor layer 100. The separating layer 104 comprises a homogeneous layer, which protects the plasmonic sensors 102. On top of the separating layer 104 a sensing layer 306 is arranged. The sensing layer 306 varies in thickness as illustrated by the thicknesses $t_1$, $t_2$, and $t_3$. The gas sensor 30 may thereby provide information pertaining to the amount of gas present in the gas sensor. This may be achieved by monitoring changes to the LSPRs of the respective plasmonic sensors $P_1$, $P_2$, and $P_3$. The plasmonic sensor $P_1$ associated to the thinnest portion of the sensing layer, i.e. having a thickness $t_1$, may be the first plasmonic sensor 102 to sense the presence of gas and also the first plasmonic sensor to be saturated or to come in adorption-desorption equilibrium with the gas. The arrangement disclosed in FIG. 3 may for instance be used to provide an early indication of the presence of a gas in a gas storage media. The arrangement is further advantageous as information about the temporal evolution of gas adsorption in the sensing material may be obtained by individually recording the LSPRs of the plasmonic sensors $P_1$, $P_2$, and $P_3$ versus time. Similarly, if the gas being sensed is removed from the sensing layer 306, and if the adsorption is reversible, information about the release (desorption) of the gas may also be obtained.

The thicknesses $t_1$, $t_2$, and $t_3$ may be 0.1 micrometer, 1 micrometer and 10 micrometer respectively, according to an embodiment of the present invention. Other thicknesses may also be used. The materials of the gas sensor 30 may be chosen from the selections of materials described in relation to the gas sensor 10.

According to other embodiments of the present invention the plasmonic sensors $P_1$, $P_2$, and $P_3$ may comprises different materials and/or have different sizes and shapes such that their LSPRs are shifted, for example in wavelength, with respect to each other such that the monitoring of the individual plasmonic sensors 102 is simplified.

Figure 4:
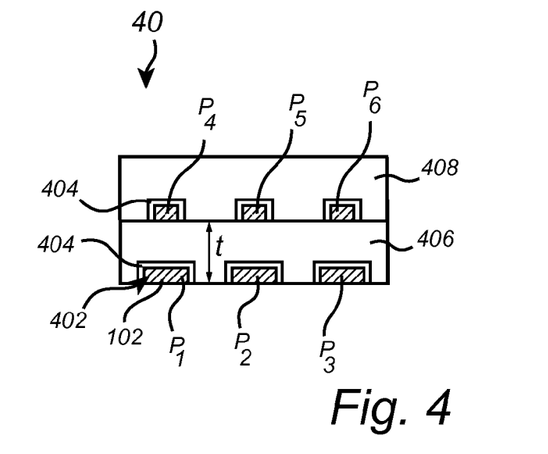
FIG. 4 is a schematic side view of a gas sensor according to one embodiment of the invention.

The separating layer may comprise a discontinuous layer. An example of such a gas sensor is illustrated in FIG. 4. In FIG. 4, a gas sensor 40 is shown which comprises a plurality 402 of plasmonic sensors 102, denoted $P_1$, to $P_6$. The separating layer 404 is arranged only in a vicinity of each of the plurality 402 of plasmonic sensors 102 such that each of the plasmonic sensors 102 is protected. The plurality 402 of plasmonic sensors 102 is arranged in two layers on top of each other at a distance set by the thickness t of a first sensing layer 406 arranged in between the two layers of plasmonic sensors 102.

To simplify the monitoring of the plasmonic sensors 102 within the two layers, the plasmonic sensors $P_1$ to $P_3$, may preferentially have LSPRs that are different spectrally to the plasmonic sensors $P_4$ to $P_6$.

It should, however, be noted that the plurality 402 of plasmonic sensors 102 may according to another embodiment have similar LSPRs. The plasmonic sensors may nevertheless be individually monitored by for instance spatially resolved imaging techniques as they are spatially separated.

A second sensing layer 408 is arranged on top of the plasmonic sensors $P_4$ to $P_6$.

Gas may penetrate both the first 406 and the second 408 sensing layers as a result of the separating layer 404 being a discontinuous layer. The gas sensor 40 may therefore provide information about the presence of gas in the first 406 and/or the second 408 sensing layers. Using the gas sensor 40 the amount of gas being present in the sensing layers 406, 408 may be described by the gas sensor 40. In other words the gas sensor 40 provides height or depth information related to the presence of gas in the sensing layers 406, 408. The height and depth information may in turn relate to different times. As an example the plasmonic sensors $P_4$ to $P_6$ may detect the presence of gas earlier than the deeper lying plasmonic sensors $P_1$ to $P_3$. The arrangement disclosed in FIG. 4 may therefore for instance be used to provide information about the amount of gas present in a gas storage media as function of distance within the gas storage media and/or at different times.

Figure 5:
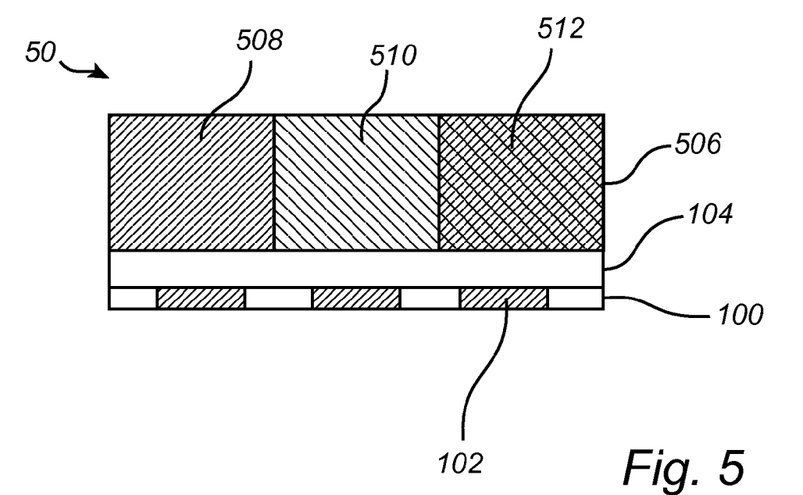
FIG. 5 is a schematic side view of a gas sensor according to one embodiment of the invention.

Now referring to FIG. 5, the gas sensor 50 may according to an embodiment of the present invention comprise a plurality of sensing layers 506. The plurality of sensing layers 506 comprises different gas permeable materials 508, 510, 512. The different materials may be different porous materials selected from the disclosed categories of porous materials or comprise different polymers. By the use of different gas permeable materials 508, 510, 512 the adsorption and penetration of gases may be different within different regions within the plurality of sensing layer 506. The gas sensor 50 may therefore be understood as a multiplexing gas sensor. In other words different regions of the gas sensor 50 are designed to sense different gases. An improved selectivity of the gas sensor 50 may thereby be obtained.

The plurality of sensing layers 506 may according to another embodiment of the invention be of the same gas permeable material, but have different porosities. An improved selectivity of a gas sensor may thereby also be obtained. Additionally, a portion of the plurality of sensing layers may for instance comprise small pores such that small gas molecules, but not larger ones, may penetrate through the sensing layer. An increase in selectivity of the gas sensor may thereby be obtained.

Figure 6:
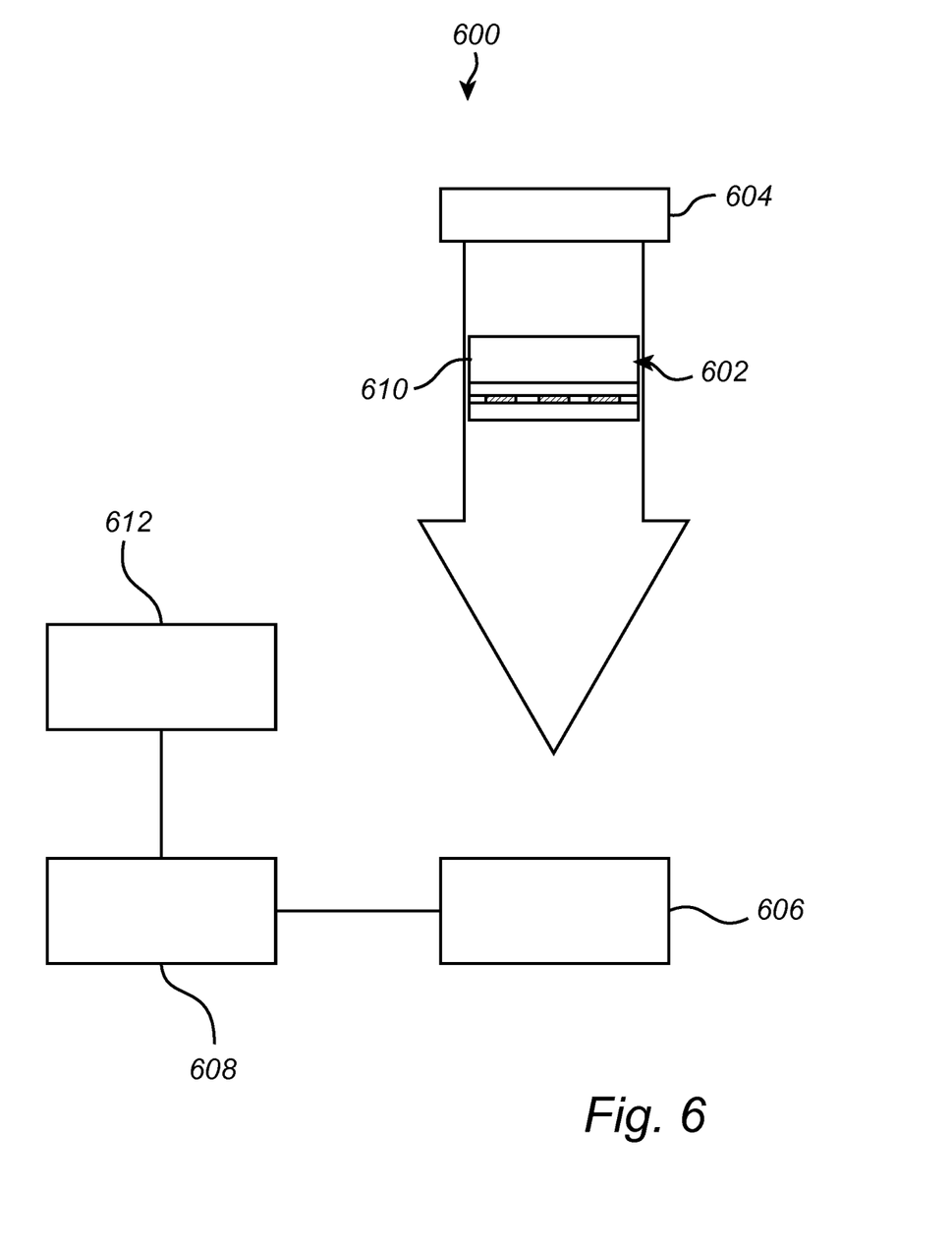
FIG. 6 is a schematic view of a gas sensing system according to one embodiment of the invention.

FIG. 6 illustrates a gas sensing system 600. The gas sensing system 600 comprises a gas sensor 602, a source 604 of electromagnetic radiation for illuminating the gas sensor 602; and a detector 606 for detecting electromagnetic radiation that is being scattered and/or reflected by and/or transmitted through the gas sensor 602. The gas sensor 602 may be any of the gas sensors disclosed above. A processing unit 608 is further provided. The processing unit 608 may be used to determine changes in the scattered and/or reflected and/or transmitted light caused by a change in the LSPR condition when the gas sensing layer 610 is exposed to a gas. The gas sensing system 600 may thereby take advantage of the reliability and robustness of the gas sensor 602 when sensing gas. An efficient system for monitoring LSPR and changes to the LSPR is furthermore provided by detecting electromagnetic radiation that is being scattered and/or reflected by and/or transmitted through the gas sensor.

It should be noted that the gas sensing system may be arranged to monitor at least one LSPR of a plasmonic sensor and/or a plurality of plasmonic sensors by using spatially and/or spectrally resolved spectroscopic and/or imaging techniques.

The gas sensing system may further comprise a temperature and/or pressure sensor 612. This is advantageous as independent measurements of the temperature and/or the pressure may be used to gain further information about the processes such as adsorption, desorption, oxidation and catalytic reactions occurring within the sensor and/or in the environment where the gas sensing system 600 is used.

The source 604 of electromagnetic radiation for illuminating the gas sensor 602 may be a broad band illumination source such as white light comprising electromagnetic radiation in the ultraviolet to infrared wavelength range. Such an illumination source provides efficient excitation and spectroscopic analysis of the LSPRs of the plasmonic sensor 602. The source 604 of electromagnetic radiation further makes it possible to use conventional optical components such as lenses and mirrors, and allows for simple and less costly instrumentation. As an example standard silicon detectors may be used to detect the LSPRs and changes to the LSPRs.

The source 604 of electromagnetic radiation may also provide monochromatic light, which may be obtained by using a broadband source and optical filters or monochromators, or a narrow band light emitting diode or a laser.

Figure 7A:
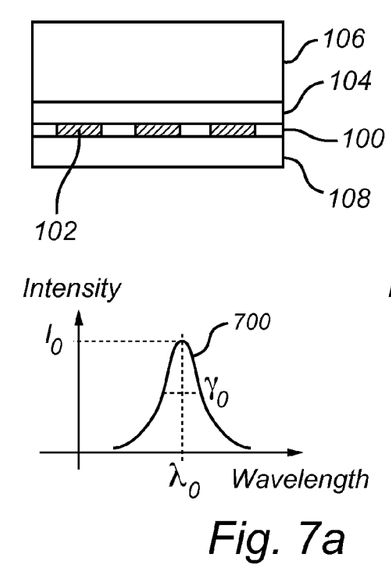
FIGS. 7a and 7b illustrate gas sensing using a gas sensor according to one embodiment of the invention.
Figure 7B:
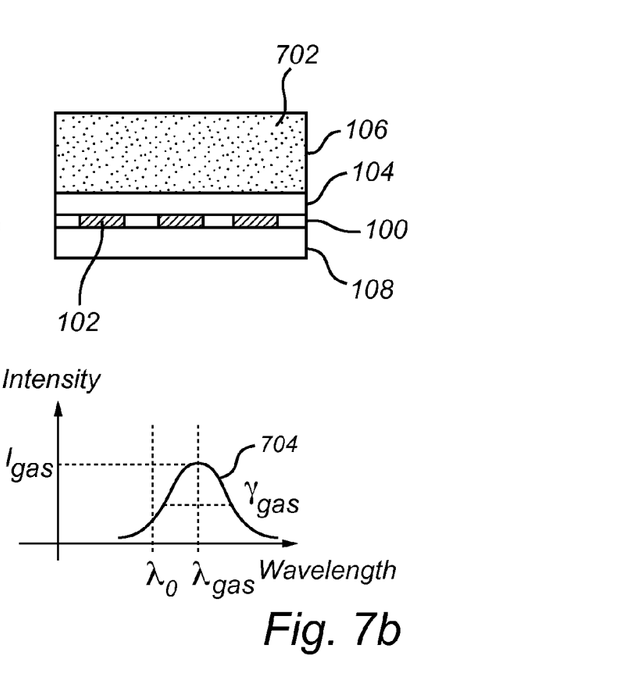

FIGS. 7a and 7b illustrate schematically how the presence of a gas is sensed by the sensing system 600 disclosed in FIG. 6. FIG. 7a illustrates the gas sensor 602 described above without the presence of a gas. Using the gas system 600 light that is reflected by and/or transmitted through the gas sensor 602 is acquired by the detector 606. An extinction spectrum 700 pertaining to the excitation of LSPRs of the plasmonic sensors 102 is obtained by use of the processing unit 608 and conventional methods to, for instance, normalize light from the source 604 of electromagnetic radiation.

The extinction spectrum 700 has characteristic features resulting from the choice of plasmonic sensors 102 and the materials used in the gas sensor 602. The extinction spectrum 700 may be described by parameters such as the centre wavelength $\lambda_0$, and the peak intensity $I_0$, and the full width at half maximum $\gamma_0$ of the spectrum. The full width at half maximum $\gamma_0$ is for instance related to the damping of the LSPR of the plasmonic sensors 102. The parameters may be determined by the processing unit 600 by analysing the extinction spectrum 700.

FIG. 7b illustrates the same gas sensor 602 described above but now with the presence of a gas 702 in the sensing layer 106. As a result of the presence of the gas an extinction spectrum 704 is instead obtained, as illustrated in FIG. 7b. In this example the extinction spectrum 704 has a centre wavelength $\lambda_{gas}$, and the peak intensity $I_{gas}$, and the full width at half maximum $\gamma_{gas}$ which all differ from those of spectrum 700. By detecting at least one of the differences between the two extinction spectra 700 and 704 the presence of the gas is sensed. A person skilled in the art realizes that other type of optical process such as scattering and absorption may instead be monitored in order to detect the gas. It should be noted that in other embodiments only one of the disclosed changes to the optical properties of the plasmonic sensors may be present which may correspond to a change of at least one of a spectral shift of resonance frequency, an amplitude shift, i.e. a change in magnitude, of optical cross-section, and a change of damping of the LSPR condition.

Figure 8:
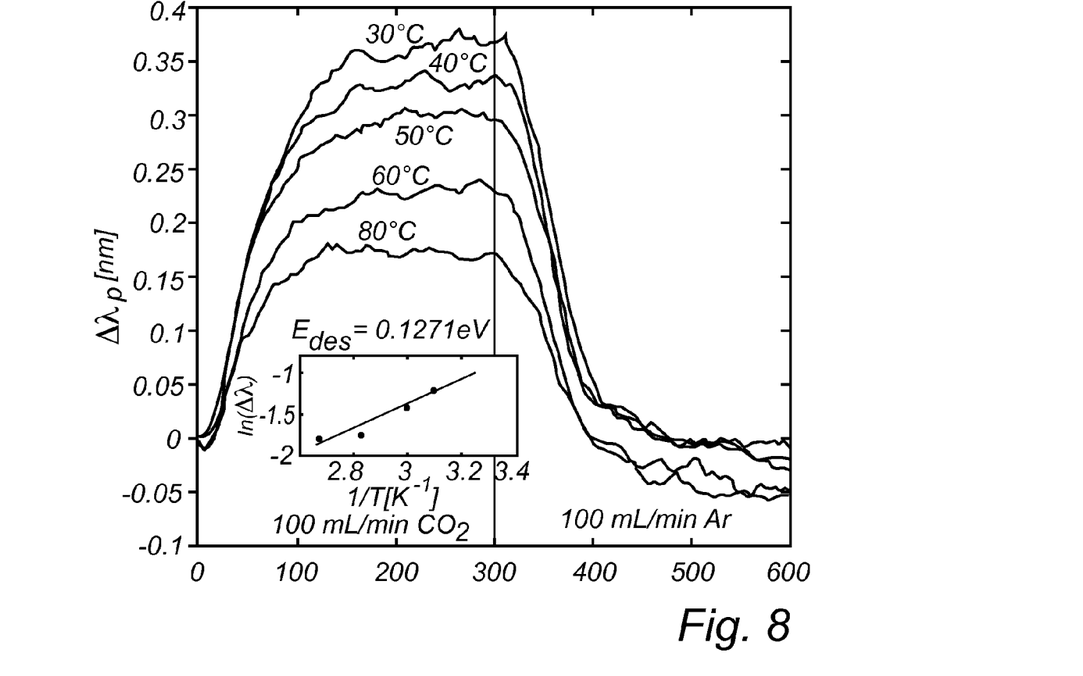
FIG. 8 is illustrates sensing of carbon dioxide using a gas sensor according to one embodiment of the invention.

FIG. 8 illustrates sensing of carbon dioxide using a gas system according to the present invention. A carbon dioxide capture measurement was performed using a micrometer thick porous titanium dioxide sensing layer. A number of loading-unloading cycles were performed at various carbon dioxide partial pressures and temperatures. The adsorption (desorption) of carbon dioxide onto the titanium oxide was measured by identifying an increase (decrease) of the peak position $\Delta\lambda_p$ of a LSPR originating from the used gas sensor. From the results shown in FIG. 8 a distinctive negative relation of carbon dioxide adsorbed with increased temperature. First order Langmuir adsorption-desorption kinetics analysis was also done to obtain the binding/desorption energy $E_{des}$ of the system of 0.1271 eV, see inset FIG. 8 This value falls within the DFT-calculated value for $CO_2$ binding on titanium dioxide showing the reliability of the gas sensing system. Another way to measure the binding energy, which was used with similar result, was to measure the total LSPR shift as a function of sensor temperature and gas concentration (partial pressure), i.e. to use so called adsorption-desorption equilibrium coverages to calculate the binding/desorption energy.

Next, sensing of hydrogen gas will be discussed. As described above a gas sensor may comprise a separating layer which is arranged to only protect a plasmonic sensor from being in direct contact with the sensing layer, i.e. the separating layer allows at least one gas to come in direct contact with the plasmonic sensor. Increased selectivity of the gas sensor may thereby be achieved. The separating layer may thereby be gas permeable to the at least one gas.

The plasmonic sensor of the gas sensor may comprise an alloy comprising Au and Pd. The plasmonic sensor may be formed by stacking a layer of Au and a layer of Pd, using for example hole-mask colloidal lithography, and annealing the stacked layers of Au and Pd such that an PdAu alloy is formed. The annealing promotes mixing and at least a partial alloying between the Au and the Pd from the respective stacked layers. The mixture of Pd and Au is advantageous for sensing hydrogen gas. This stems from that Pd absorbs hydrogen such that an improved hydrogen uptake is achieved in the plasmonic sensor resulting in at least a change of the LSPR condition for the plasmonic sensor. For a Pd containing plasmonic sensor the resonance frequency for the LSPR condition typically shifts linearly with the concentration of hydrogen inside the Pd.

The presence of Au in the PdAu alloy increases the stability of the plasmonic sensor compared to plasmonic sensors consisting of Pd. A more durable plasmonic sensor is thereby obtained by introducing Au in the plasmonic sensor.

An increased Au content in the PdAu alloy further reduces hysteresis in the charge/discharge cycle for a plasmonic sensor comprising the PdAu alloy. An improved sensitivity and reliability for sensing hydrogen may thereby be obtained.

The kinetics of the hydrogen uptake is further improved by increasing the amount of Au in the PdAu alloy as the response/recovery time of the plasmonic sensor is increased. Hence a faster gas sensor may be achieved.

Preferably the amount of Au in the $Pd_{1-x}Au_x$ alloy is in the range of 15 to 35%, i.e., x=15-35.

The annealing temperature for annealing a plasmonic sensor comprising stacked layers of Au and Pd may be in the range 200° C. to 600° C. Preferably, annealing is performed for about 2 hours at a temperature of about 500° C. Such an annealing achieves a complete or near to complete intermixing of the Au and Pd in the plasmonic sensor.

The skilled person in the art understands that other metals may be used for providing plasmonic sensors comprising a metal alloy and that more than two metal layers may be used for forming the metal alloy.

Figure 9:
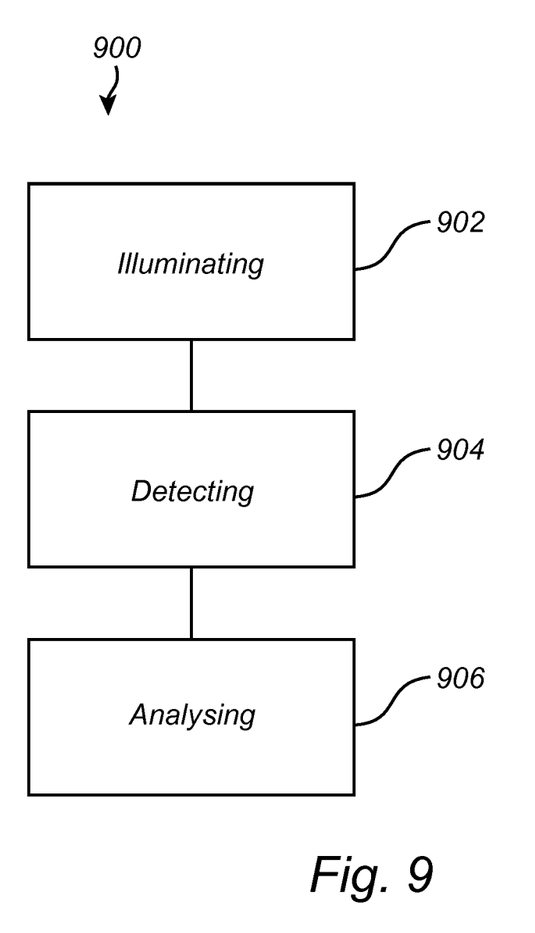
FIG. 9 is a schematic flow chart, showing a method for sensing a presence of a gas according to an embodiment of the present invention.

FIG. 9 illustrates a flow chart 900 illustrating a method for sensing a presence of a gas using any of the gas sensors disclosed. The method comprises illuminating 902 the gas sensor with electromagnetic radiation from a electromagnetic radiation source, detecting 904, via a electromagnetic radiation detector, electromagnetic radiation that is being reflected by and/or transmitted through the gas sensor, and analysing 906, by means of a processing unit, changes in the scattered and/or reflected and/or transmitted electromagnetic radiation caused by a modification of the localized surface plasmon resonance condition when the sensing layer is exposed to the gas.

In general, features of the method according to the present invention provide similar advantages as discussed above in relation to the gas sensors and the gas sensing system described above.

The person skilled in the art realizes that the present invention by no means is limited to the preferred embodiments described above. On the contrary, many modifications and variations are possible within the scope of the applied claims.

Additionally, variations to the disclosed embodiments can be understood and effected by the skilled person practicing the claimed invention, from study of the drawings, the disclosure, and the appended claims. Moreover, in the drawings and specifications, there have been disclosed preferred embodiments and examples of the invention and, although specific term are employed, they are used in a generic and descriptive sense only, and not for the purpose of limitation, the scope of the invention being set forth in the following claims. In the claims, the word "comprising" does not exclude other elements or steps, and the indefinite article "a" or "an" does not exclude a plurality.

The invention claimed is:

1. An indirect gas sensor comprising,
    a sensor layer comprising a plasmonic sensor provided so as to allow, upon illumination with electromagnetic radiation, a localized surface plasmon resonance condition,
    a sensing layer comprising a gas permeable material that, when exposed to a gas, modifies the localized surface plasmon resonance condition,
    a gas impermeable separating layer arranged in between the sensor layer and the sensing layer, such that the plasmonic sensor is separated from the sensing layer.

2. An indirect gas sensor according to claim 1, wherein the gas permeable material comprises a porous material.

3. An indirect gas sensor according to claim 2, wherein the porous material is selected from a group of porous materials consisting of macroporous, mesoporous, microporous, and hybrid porous materials.

4. An indirect gas sensor according to claim 1, wherein the gas permeable material comprises a polymer.

5. An indirect gas sensor according to claim 1, wherein the gas comprises a gas selected from a group consisting of carbon oxides, nitrogen oxides, oxygen, ozone, nitrogen, hydrogen water vapour, sulphur oxides, hydrocarbons, ammonia, ethane, and halogens.

6. An indirect gas sensor according to claim 1, wherein the modification of the localized surface plasmon resonance condition results in a change of at least one of a spectral shift of resonance frequency, an amplitude shift of optical cross-section, and a change of damping of the localized surface plasmon resonance condition.

7. An indirect gas sensor according to claim 1 wherein the plasmonic sensor is a disk, rod, wire, ellipse, polygon, triangle, sphere, cube, star, hole in thin metal film, nanoshell, core-shell particle, nanorice or nanoring.

8. An indirect gas sensor according to claim 1 wherein the plasmonic sensor comprises a semiconductor and/or a metal.

9. An indirect gas sensor according to claim 8 wherein the metal is selected from a group consisting of Ag, Au, Cu, Al, Mg, Ni, Pd and Pt, or alloys comprising at least one metal selected from the group.

10. An indirect gas sensor according to claim 1 wherein the gas impermeable separating layer comprises a material selected from a group of materials comprising a metal oxide, a metal carbide or a metal nitride, a semiconductor oxide or a semiconductor nitride or a semiconductor carbide, an insulator, and a polymer.

11. An indirect gas sensor according to claim 1 wherein the gas impermeable separating layer has a thickness in the range of 0.5 to 150 nm.

12. An indirect gas sensor according to claim 1, further comprising a plurality of plasmonic sensors.

13. An indirect gas sensing system comprising:
the indirect gas sensor according to claim 1;
a source of electromagnetic radiation for illuminating the indirect gas sensor; and
a detector for detecting electromagnetic radiation that is being scattered and/or reflected by and/or transmitted through the indirect gas sensor,
a processing unit arranged to determine changes in the scattered and/or reflected and/or transmitted electromagnetic radiation caused by a change in the localized surface plasmon resonance condition when the sensing layer is exposed to a gas.

14. An indirect gas sensing system according to claim 13, further comprising a temperature and/or pressure sensor.

15. A method for sensing a presence of a gas, the method comprising:
illuminating an indirect gas sensor with electromagnetic radiation from an electromagnetic radiation source, wherein the indirect gas sensor comprises:
a sensor layer comprising a plasmonic sensor provided so as to allow, upon illumination with electromagnetic radiation, a localized surface plasmon resonance condition,
a sensing layer comprising a gas permeable material that, when exposed to a gas, modifies the localized surface plasmon resonance condition, and
a gas impermeable separating layer arranged in between the sensor layer and the sensing layer, such that the plasmonic sensor is separated from the sensing layer;
detecting, via an electromagnetic radiation detector, electromagnetic radiation that is being scattered and/or reflected by and/or transmitted through the indirect gas sensor; and
analysing, by a processing unit, changes in the scattered and/or reflected and/or transmitted electromagnetic radiation caused by a modification of the localized surface plasmon resonance condition when the sensing layer is exposed to the gas.

\* \* \* \* \*